US010485792B2

United States Patent
Friedman et al.

(10) Patent No.: US 10,485,792 B2
(45) Date of Patent: Nov. 26, 2019

(54) SUSTAINED RELEASE DELIVERY SYSTEMS FOR THE PREVENTION AND TREATMENT OF HEAD AND NECK CANCERS

(75) Inventors: Michael Friedman, Jerusalem (IL); Rakefet Czernimski, Mevaseret-Tzion (IL); Silvio Gutkind, Potomac, MD (US); Doron Steinberg, Jerusalem (IL); Irith Gati, Mevaseret Zion (IL); Zakhar Nudelman, Netanya (IL)

(73) Assignees: HADASIT MEDICAL RESEARCH SERVICES & DEVELOPMENT LIMITED, Jerusalem (IL); YISSUM RESEARCH DEVELOPMENT COMPANY OF THE HEBREW UNIVERSITY OF JERUSALEM LTD., Jerusalem (IL); THE UNITED STATES OF AMERICA AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 13/391,756

(22) PCT Filed: Aug. 25, 2010

(86) PCT No.: PCT/IL2010/000694
§ 371 (c)(1),
(2), (4) Date: Oct. 5, 2012

(87) PCT Pub. No.: WO2011/024168
PCT Pub. Date: Mar. 3, 2011

(65) Prior Publication Data
US 2013/0018069 A1    Jan. 17, 2013

Related U.S. Application Data

(60) Provisional application No. 61/237,062, filed on Aug. 26, 2009.

(51) Int. Cl.
| | | |
|---|---|---|
| *A61K 31/436* | (2006.01) | |
| *A61K 9/00* | (2006.01) | |
| *A61K 9/20* | (2006.01) | |
| *A61K 9/70* | (2006.01) | |

(52) U.S. Cl.
CPC ............ *A61K 31/436* (2013.01); *A61K 9/006* (2013.01); *A61K 9/2054* (2013.01); *A61K 9/7015* (2013.01)

(58) Field of Classification Search
CPC combination set(s) only.
See application file for complete search history.

(56) References Cited

U.S. PATENT DOCUMENTS

| | | |
|---|---|---|
| 6,197,331 B1 * | 3/2001 | Lerner et al. .................. 424/448 |
| 2005/0132825 A1 | 2/2005 | Metcalf |
| 2007/0104783 A1 | 5/2007 | Domb |
| 2007/0185150 A1 | 8/2007 | Bedrosian |
| 2011/0200556 A1 | 8/2011 | Gutkind et al. |

FOREIGN PATENT DOCUMENTS

| | | |
|---|---|---|
| CN | 101361703 A | 2/2009 |
| WO | 2005/016321 A1 | 2/2005 |
| WO | 2006/072940 A2 | 7/2006 |
| WO | 2006/094507 A1 | 9/2006 |
| WO | 2008/098634 A1 | 8/2008 |
| WO | 2010/022243 A1 | 2/2010 |

OTHER PUBLICATIONS

Dow ( ETHOCEL Ethylcellulose Polymers Technical Handbook, 2005, pp. 1-28).*
International Search Report of PCT/IL2010/000694 dated Apr. 21, 2011.
Wang et al., F., "Current and Potential Inflammation Targeted Therapies in Head and Neck Cancer", Current Opinion in Pharmacology, Elsevier Science Publishers, NL, vol. 9, No. 4, pp. 389-395, Aug. 1, 2009 XP026587071.
Czerninski et al., Rakefet, "Targeting Mammalian Target of Rapamycin by Rapamycin Prevents Tumor Progression in an Oral-Specific Chemical Carcinogenesis Model", Cancer Prevention Research American Association for Cancer Reserach, United States, vol. 2, No. 1, pp. 27-36, Jan. 1, 2009 XP009125903.
Salamat-Miller et al, N., "The Use of Mucoadhesive Polymers in Buccal Drug Delivery", Advanced Drug Delivery Reviews, Elsevier BV, Amsterdam, NL, vol. 57, No. 11, pp. 1666-1691, Nov. 3, 2005 XP025284004.
Czerninski et al., Rakefet, "A Novel Substained-Release Clotrimazole Varnish for Local Treatment of Oral Candidiasis", Clinical Oral Investigations, Springer, Berlin, DE, vol. 14, No. 1, pp. 71-78, Apr. 29, 2009 XP019783631.
Sudhakar et al., "Buccal bioadhesive drug delivery—a promising option for orally less efficient drugs", Journal of Controlled Release, Elsevier, Amsterdam, NL, vol. 114, No. 1, pp. 15-40, Aug. 10, 2006 XP005586185.

(Continued)

*Primary Examiner* — Kathrien A Cruz
(74) *Attorney, Agent, or Firm* — Browdy and Neimark, PLLC (57) ABSTRACT

The present invention discloses a method of treating a head and neck cancer or preventing the development of pre-malignant lesions to this cancer, by administering locally to the oral cavity, a sustained release drug delivery system comprising a drug for the treatment of this cancer or for the prevention of said lesions, and at least one polymer, such that said system is attached to a surface in the oral cavity and remains attached thereto for at least 1 hour, accompanied by release of the drug and maintaining an effective therapeutic concentration thereof in the cavity, for at least 1 hour. Further are disclosed a sustained release drug delivery system and a liquid precursor varnish composition to this system.

15 Claims, 3 Drawing Sheets

(56) References Cited

OTHER PUBLICATIONS

Soria, A. et al., "Treatment of Refractory Oral Erosive Lichen Planus with Topical Rapamycin: 7 Cases", Dermatology, vol. 218, No. 1, pp. 22-25, Nov. 10, 2008 XP009142920.
Amornphimoltham et al., Mammalian Target of Rapamycin, a Molecular Target in Squamous Cell Carcinomas of the Head and Neck, Cancer Res, 65:9953-9961 (2005).
Tabernero et al., Dose- and Schedule-Dependent Inhibition of the Mammalian Target of Rapamycin Pathway With Everolimus: A Phase I Tumor Pharmacodynamic Study in Patients With Advanced Solid Tumors, Journal of Clinical Oncology, 26(10):1603-1610; 5350 (2008).
Ritger et al., A Simple Equation for Description of Solute Release I. Fickian and Non-Fickian Release From Non-Swellable Devices in the Form of Slabs, Spheres, Cylinders or Discs, Journal of Controlled Release 5:23-36 (1987).
Bissler et al., Sirolimus for Angiomyolipoma in Tuberous Sclerosis Complex or Lymphangioleiomyomatosis, N Engl J Med, 358(2):140-151 (2008).
Nudelman et al., Levels of Sirolimus in Saliva vs. Blood—the Rationale of Topical Oral Use for Oral Malignancy, Anticancer Research, 33:661-664 (2013).
Nudelman et al., Levels of sirolimus in saliva and blood following oral topical sustained-release varnish delivery system application, Cancer Chemother Pharmacol, (2015).

* cited by examiner

SUSTAINED RELEASE DELIVERY SYSTEMS FOR THE PREVENTION AND TREATMENT OF HEAD AND NECK CANCERS

With approximately 500,000 new cases annually, squamous cell carcinomas of the head and neck (HNSCC), the vast majority of which arise in the oral cavity, represent the sixth most common cancers in the world. This disease results in nearly ~11,000 deaths each year in the United States alone. The five-year survival rate after diagnosis for HNSCC remains considerably low (approximately 50%). This poor prognosis of oral squamous cell carcinoma (OSCC) patients is likely due to the fact that most patients are diagnosed at advanced disease stages, and often fail to respond to available treatment options.

The intervention at early stages of the oral carcinogeneis can improve survival while prevention of tumor development or tumor progression carries a promising outcome. Unlike some other solid tumors, early lesion in the oral cavity, currently termed as "potentially malignant disorders" can be detected clinically, without any invasive technology. The rate of malignant transformation of those lesions is in the range of 10-40% and depends on the epithelial changes and the duration of the follow up. Unfortunately, although detection methods are improving, there are no advances in intervention approaches in order to prevent cancer development in those lesions. The recommended treatment approaches to oral dysplasia or potentially malignant disorders are avoidance of risky behavior (such as smoking, alcohol consumption or sun exposure in lip carcinoma), encouraging healthy nutrition although there is no good evidence that these actions can significantly reduce malignant transformation and a close follow up of the oral cavity, in order to diagnose any newly developed lesion which is called "watchful waiting". Removal of the high-risk lesion either by scalpel or laser wasn't proved to be fully preventive of malignant transformation (Van der Waal I. management. Oral Oncol. 2010 June; 46(6):423-5).

Previous studies using chemotherapy, in order to prevent cancer development in premalignant lesions showed variable results and failed to show long term success. (Lodi G, Sardella A, Bez C, Demarosi F, Carrassi A. Interventions for treating oral leukoplakia. Cochrane Database Syst Rev 2006; 4: CD001829.)

Sirolimus (Rapamycin) is a macrocyclic lactone with antifungal and antibiotic properties isolated from *Streptomyces hygroscopicus* during the 70's. Studies of rapamycin properties in yeast led to the discovery of TOR (Target of Rapamycin) and its mammalian analogue, mTOR. mTOR is a central regulator of cell growth and proliferation in response to environmental stimuli such as growth factors or nutrients. It has become known that mTOR blocking strategy is very promising for certain tumors management and particularly for OSCC and potential malignant disorders.

Antiproliferative effects of rapamycin and analogues have been demonstrated on numerous cell types, explaining the development of these drugs in clinical practice: as immunosuppressive drugs in solid organ transplantation, and for the prevention of restenosis after coronary angioplasty. In oncology these antiproliferative effects are evaluated as treatment of various types of cancers.

Rapamycin is one of the leading agents for the prevention and treatment of OSCC. The recent findings (Czerninski R. Patel V, Amornphimoltham P, Molinolo A. A and Gutkind J S. *Targeting Mammalian Target of Rapamycin by Rapamycin Prevents Tumor Progression in an Oral-Specific Chemical Carcinogenesis Model*; in: Cancer Prev. Res. 2009 2: 27-36) show we show that the inhibition of mTOR by the chronic administration of rapamycin halts the malignant conversion of pre-cancerous lesions and promotes the regression of advanced carcinogen-induced SCCs.

Alongside with the high potency systemic administration of rapamycin characterized by some typical side effects including: peripheral edema, hypertriglyceridemia, hypertension, hypercholesterolemia, creatinine increased, constipation, abdominal pain, diarrhea, headache, fever, urinary tract infection, anemia, nausea, arthralgia, pain, and thrombocytopenia.

For example, a study was performed using topical rapamycin solution for the treatment of Oral Lichen Planus. (A. Soria a S. Agbo-Godeau b A. Taïeb c C. Francès a *Treatment of Refractory Oral Erosive Lichen Planus with Topical Rapamycin: 7 Cases*, in: Dermatology. 2009; 218 (1):22-5). The study involved direct topical application of rapamycin to the diseases regions. During the study tingling or burning sensations were encountered after rapamycin had first been applied. Nevertheless, a tendency for progressive decrease in this side effect was observed. The study has also shown negligible blood levels and respectively no systemic adverse effects were encountered.

Furthermore, WO 2010/022243 disclosed a method for preventing the development of HNSCC in mammals by systemic administration of mTOR inhibitors, such as rapamycin, to the mammal. In another example, lichen planus was treated with rapamycin mouth solution (Soria, A., et al., *Treatment of refractory oral erosive lichen planus with topical rapamycin: 7 cases*. Dermatology, 218(1): p. 22-5 (2009). However, in both of these cases the active agent does not stay in the oral cavity for a prolonged period, and is easily washed away.

Moreover, these systems have additional disadvantages, such as non-optimized treatment, due to low and short-timed therapeutic levels at the site of action, patient compliance is relatively low to a treatment method which requires several applications per day. Yet further, as described above, the common uses of sirolimus and its analogues is associated with adverse effects, due to its relatively high concentrations during application.

The present inventors have previously taught slow released oral compositions for a variety of local uses, such as the treatment of oral fungal or bacterial infections, treatment of dental hypersensitivity and plaque removal (see for example U.S. Pat. Nos. 5,438,076, 5,989,522 and 5,139, 768).

It would have been advantageous to develop a sustained release drug delivery system comprising a drug for the treatment and prevention of head and neck cancers, such as oral cancers, thereby circumventing the disadvantages of presently known methods of treating and/or preventing HNSCC and similar conditions.

The present inventors have now successfully prepared slow released formulations of sirolimus (rapamycin), suitable for use in the oral cavity, and have surprisingly found that the local delivery of rapamycin, to the oral cavity, for prolonged periods of time, creates local concentrations of the drug in that cavity and thus rendering it suitable for the treatment of head and neck cancers, or suitable for preventing the progression of oral lesions ("potentially malignant disorders") to these cancers, while minimizing undesired systemic side effects.

Thus, according to one aspect of the invention, there is provided a method of treating a head and neck cancer or preventing the development of pre-malignant lesions to this cancer, the method comprising: administering locally to the oral cavity, a sustained release drug delivery system comprising:

a) a drug for the treatment of this cancer or for the prevention of these lesions, and
b) at least one polymer, such that the system is attached to a surface in the oral cavity and remains attached thereto for at least 1 hour, accompanied by release of the drug and maintaining an effective therapeutic concentration thereof in the cavity, for at least 1 hour.

The term "head and neck cancer" describes any cancer that arises in the head or neck region. In general, it is a group of cancers originating from the upper aerodigestive tract, including the lip, oral cavity, nasal cavity, paranasal sinuses, salivary glands, pharynx, and larynx.

Most head and neck cancers begin in the squamous cells that line the structures found in the head and neck and are therefore termed squamous cell carcinomas (SCCHN). Because of this, head and neck cancers are often referred to as squamous cell carcinomas. Some head and neck cancers begin in other types of cells. For example, cancers originating from glandular cells are called adenocarcinomas.

Cancers of the head and neck are further identified by the area in which they begin: cancers of the oral cavity, cancers of the salivary glands, cancer of the paranasal sinuses and nasal cavity, cancers of the pharynx and cancers of the larynx.

The term "oral cavity" includes the lips, the pharynx, the tongue, the gums (gingiva), the lining inside the cheeks and lips (buccal mucosa), the bottom (floor) of the mouth under the tongue, the bony top of the mouth (hard palate), the soft palate and the small area behind the wisdom teeth (retromolar area).

The salivary glands include the glands under the tongue lower jaw (submandibular and sublingual), in front of the ears (parotid gland), as well as in other parts of the upper digestive tract-minor salivary glands.

The term "paranasal sinuses" refers to the small hollow spaces in the bones of the head surrounding the nose. The term "nasal cavity" refers to the hollow space inside the nose.

The term "pharynx" refers to the hollow tube that starts behind the nose and leads to the esophagus and the trachea. The pharynx has three parts:

Nasopharynx, the upper part of the pharynx, behind the nose;
Oropharynx, the middle part of the pharynx, which includes the soft palate, the base of the tongue and the tonsils;
Hypopharynx, the lower part of the pharynx.

The term "larynx" is also known as the voicebox, and is the passageway formed by cartilage below the pharynx in the neck. It contains the vocal cords and the epiglottis.

Thus, the term "oral cancer" encompasses all malignancies that originate in the oral tissues, in particular to cancers located in any part of the mouth, including the lips, gum tissue (gingival), tongue, cheek lining (buccal mucosa) and the soft or hard palate, and floor of the mouth, or in the pharynx, the top part of the throat.

Sometimes, squamous cancer cells are also found in the lymph nodes of the upper neck.

The term "head and neck cavity" refers to a cavity within the head and neck area, that may be effected by a head and neck cancer. This may include in addition to the oral cavity also the nasal cavity, and the pharynx. It is expected that the method of the present invention shall be suitable to treat cancers in these cavities as well.

According to a preferred embodiment, the oral cancer is a carcinoma.

According to a further specific embodiment of the invention, the carcinoma is a head and neck squamous cell carcinoma (HNSCC).

According to yet another embodiment of the invention, the oral cancer is a melanoma cancer.

The term "pre-malignant lesions" as described herein refers to a lesion that, while not cancerous, has potential for becoming cancerous. It also includes the term "pre-malignant disorders" or "potentially malignant disorders". In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia.

The term "administering locally" refers to a method of administration which is limited to a specific organ or cavity to be treated, in contrast to a systemic administration which does not target a specific area.

The term "sustained release drug delivery system" refers to release of the drug or active agent from the drug delivery system so that it becomes available for bio-absorption in the subject, primarily in the specific head and neck cavity of the subject where it is locally administered, over a prolonged period of time, such as about 1 hour to 24 hours or more. In certain embodiments of the composition of the invention, that period of time will be at least about 1 hour, at least about 4 hours, at least about 6 hours, or at least about 8 hours. The term "sustained release" also encompasses what is otherwise referred to as "extended release", "controlled release", or "sustained delivery". The release rate of the active agent is primarily controlled by the properties of the materials comprising the drug delivery system, but is also influenced by the presence and quantity of carriers and/or, the drug or additional constituents, such as release modifiers.

In a preferred embodiment of the invention the method specifically addresses the treatment of oral cancer and the prevention of potentially malignant disorders leading to it. Thus, according to a preferred embodiment there is provided a method for preventing or slowing down the progression of oral lesions ("potentially malignant disorders") to oral cancer (and in particular carcinoma) comprising administering locally to the oral cavity a sustained release drug delivery system comprising a drug for the treatment of or prevention of oral cancers.

The term "oral cancer" in the context of the invention refers to carcinomas, lymphomas, sarcomas, tumor of the salivary glands and melanoma. In accordance with a preferred embodiment of the invention the tumor is oral squamous cell carcinoma (OSCC).

It should be clarified that the above-described method is not limited to the treatment of human subjects, but is just as suitable for veterinary use, for the treatment of various animals.

The term "drug for the treatment of an oral cancer or preventing or slowing progression of potentially malignant disorders to oral cancer" refers to any chemical or biological agent that is known to treat the oral cancers or prevent its progression.

Where the cancer is oral squamous cell carcinoma the drug is typically an mTOR inhibitor such as sirolimus (rapamycin) and its analogues.

The term "mTOR inhibitor" refers to a compound or ligand, or a pharmaceutically acceptable salt thereof, that inhibits cell replication by blocking the progression of the cell cycle from G1 to S. The term includes the neutral tricyclic compound rapamycin (sirolimus) and other rapamycin compounds, including, e.g., rapamycin derivatives, rapamycin analogues, other macrolide compounds that inhibit mTOR activity, and all compounds included within the definition below of the term "a rapamycin".

Sirolimus is 3S,6R,7E,9R,10R,12R,14S,15E,17E,19E,21S,23S, 26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]-oxaazacyclohentriacontine-1,5,11,28,29(4H,6H,31H)-pentone.

The term "analogues" include substituted rapamycin, e.g. rapamycin substituted in position 40 and/or 16 and/or 32. Examples of rapamycin analogues include 40-O-alkyl-rapamycin derivatives, e.g. 40-O-hydroxyalkyl-rapamycin derivatives, for example 40-O-(2-hydroxy)-ethyl-rapamycin (everolimus), rapamycin analogues which are substituted in 40 position by heterocyclyl, e.g. 40-epi-(tetrazolyl)-rapamycin (also known as ABT578),32-deoxo-rapamycin derivatives and 32-hydroxy-rapamycin derivatives, such as 32-deoxorapamycin,16-O-substituted rapamycin derivatives such as 16-pent-2-ynyloxy-32-deoxorapamycin, 16-pent-2-ynyloxy-32(S or R)-dihydro-rapamycin, or 16-pent-2-ynyloxy-32(S or R)-dihydro-40-O-(2-hydroxyethyl)-rapamycin, rapamycin analogues which are acylated at the oxygen in position 40, e.g. 40-[3-hydroxy-2-(hydroxy-methyl)-2-methylpropanoate]-rapamycin (also known as CCI779 or temsirolimus), rapamycin derivatives (also sometimes designated as rapalogs) as disclosed in WO9802441 or WO0114387, e.g. including AP23573, such as 40-O-dimethylphosphinyl-rapamycin, compounds disclosed under the name biolimus (biolimus A9), including 40-O-(2-ethoxy) ethyl-rapamycin, and compounds disclosed under the name TAFA-93, AP23464, AP23675 or AP23841; or rapamycin derivatives as e.g. disclosed in WO2004101583, WO9205179, WO9402136, WO9402385 and WO9613273.

Preferred rapamycin analogues include: 40-O-(2-hydroxyethyl)-rapamycin, and/or 32-deoxorapamycin, and/or 16-pent-2-ynyloxy-32-deoxorapamycin, and/or 16-pent-2-ynyloxy-32 (S or R)-dihydro-rapamycin, and/or 16-pent-2-ynyloxy-32 (S or R)-dihydro-40-O-(2-hydroxyethyl)-rapamycin, and/or 40-[3-hydroxy-2-(hydroxy-methyl)-2-methylpropanoate]-rapamycin (also known as CCI779) and/or 40-epi-(tetrazolyl)-rapamycin (also known as ABT578), and/or the so-called rapalogs, e.g. as disclosed in WO9802441, WO0114387 and WO0364383, AP23573, AP23464, AP23675 or AP23841, e.g. AP23573, and/or compounds disclosed under the name TAFA-93, and/or compounds disclosed under the name biolimus.

More preferably a rapamycin analogue is selected from the group consisting of: 40-O-(2-hydroxyethyl)-rapamycin (also known as everolimus), and/or 32-deoxorapamycin, and/or 16-pent-2-ynyloxy-32-deoxorapamycin, and/or 16-pent-2-ynyloxy-32 (S or R)-dihydro-rapamycin, and/or 16-pent-2-ynyloxy-32 (S or R)-dihydro-40-O-(2-hydroxy-ethyl)-rapamycin, and/or 40-[3-hydroxy-2-(hydroxy-methyl)-2-methylpropanoate]-rapamycin (also known as CCI779 or temsirolimus) and/or 40-epi-(tetrazolyl)-rapamycin (also known as ABT578), and/or AP23573, such as 40-O-(2-hydroxyethyl)-rapamycin.

It has been established that the drug constitutes from about 10% by weight to about 90% by weight of the dry composition of the dry composition. The exact amount depends on the specific requirements, application and additional ingredients, and can be determined by any person skilled in the art.

In addition to the drug described herein, the sustained release drug system also used for the method described herein includes at least one polymer.

The term "polymer" includes any polymer which is suitable to form a matrix incorporating the drug and additional ingredients or additives in it, such that the polymer determines the rate of drug release from this matrix. Polymers capable of forming a matrix suitable for the purpose of the present invention include either non-degradable hydrophobic polymers, or hydrophilic mucoadhesive polymers, or any combination thereof, depending on the exact application.

The term "non-degradable hydrophobic polymers" means that the polymers do not degrade or break down in contact with the surface of the oral cavity where they are to be attached. As the oral environment is aqueous in nature, suitable polymers would need to be hydrophobic. They would also need to be both stable and non-degradable under the in-vivo conditions.

Non-limiting examples of non-degradable hydrophobic polymers are ethyl cellulose, Silicone rubber, polyethylene, polylactic acid, polymethylmethacrylate, gelatin and cross-linked derivatives, polyvinyl chloride, polyvinyl acetate, polyurethane and any combinations thereof.

Preferably, the hydrophobic polymer is ethyl cellulose (EC). It should be noted that EC has many grades, and the choice of the appropriate grade is dependant on the total composition and expected use.

The formulations may further include thermosensible polymers such as poloxamers (poloxamer 407) and pH sensitive polymers such as Eudragit E.

Non limiting examples of mucoadhesive polymers include sodium carboxymethyl cellulose, poly(acrylic acid), tragacanth, poly(methyl vinyl ether co-maleic anhydride), poly(ethylene oxide), methyl cellulose, sodium alginate, hydroxypropylmethylcellulose, karya gum, methylethylcellulose, soluble starch, gelatin, pectin, poly(vinyl pyrrolidone), poly(ethylene glycol), poly(vinyl alcohol), poly(hydroxyethylmethacrylate), hydroxypropyl cellulose and combinations thereof.

It has been established that the polymer constitutes from about 10% by weight to about 90% by weight of the dry composition. The exact amount depends on the specific requirements and application.

Additional ingredients may be added to enhance the properties of the system. These may include release enhancers, plasticizers, taste modifiers etc, as described in detail below.

The term "release enhancer" as used in the invention designates compounds that enhance the release of the drug from the polymeric matrix in which it is incorporated.

As used herein, the term "plasticizer" refers to a material that may be incorporated into the sustained release drug delivery system in order to decrease the glass transition temperature and/or the melt viscosity of the polymer forming the matrix, by increasing the free volume between the polymeric chains.

Both Release Enhancers and plasticizers, include, but are not limited to, water; citrate esters, (e.g., triethylcitrate, triacetin); poly(alkylene oxides) (e.g., poly(ethylene glycols), poly(propylene glycols), poly(ethylene/propylene glycols)); glycerol, pentaerythritol, glycerol monoacetate, diacetate or triacetate; glycerine, propylene glycol; sodium diethyl sulfosuccinate and any combinations thereof. Additional examples of plasticizers can be found in The Handbook of Pharmaceutical Additives, Ash et al., Gower Publishing (2000).

As noted above, one of the preferred hydrophobic polymers used in the present invention is ethyl cellulose. Specific plasticizers compatible with ethyl cellulose include, but are not limited to:

Phosphate Esters, such as tricresyl phosphate, triethyl phosphate and triphenyl phosphate;

Phthalate Esters, such as methyl phthalate, cyclohexyl butyl phthalate, cyclohexyl ethyl phthalate, cyclohexyl methyl phthalate, diamyl phthalate, dibutyl phthalate, dicapryl phthalate, dicyclohexyl phthalate, diethyl phthalate, diisobutyl carbinyl phthalate, diisopropyl phthalate, dimethyl phthalate, dinonyl phthalate, dioctyl phthalate, diphenyl phthalate, diethoxyethyl phthalate, dibutoxyethyl phthalate, dimethoxyethyl phthalate;

Miscellenius Esters, such as abalyn methyl abietate, acetyl tributyl citrate, acetyl triethyl citrate, diisooctyl adipate, amyl oleate, butyl ricinoleate, benzyl benzoate, butyl and glycol esters of fatty acids, butyl diglycol carbonate, butyl oleate, butyl stearate, di($\beta$-methoxyethyl)adipate, dibutyl sebacate, dibutyl tartrate, diisobutyl adipate, dihexyl adipate, triethylene glycol di(2-ethyl butyrate), polyethylene glycole di(2-ethyl hexoate), monomeric polyethylene esters, hydrogenated methyl esters of rosin, methoxyethyl oleate, butoxyethyl stearate, glycerol tributyrate, triethylene glycol dipelargonate, beta-(p-tert-amylphenoxy)ethanol, beta-(p-tert-butylphenoxy)ethanol, beta-(p-tert-butylphenoxyethyl)acetate, bis($\beta$-p-tert-butylphenoxydiethyl)ether, camphor, cumar R-3, R-14, diamyl phthalate, diamylphenoxy ethanol, diphenyl oxide;

Amides, such as bis(dibutyl) adipamide, dibutyllaurамide, diethyldiphenylurea;

Mineral oils, such as refined mineral oils, white mineral oils, lubricating oils etc.;

Fatty Acids such as linseed, oleic, ricinoleic, stearic etc.;

Fatty Alcohols such as cetyl, myristyl, stearyl etc.;

Vegetable oils such as castor oil, corn oil, cottonseed oil, linseed oil, soybean oil, etc.

Miscellaneous types such as Abitol E technical hydroabietyl alcohol, Beckolin, chlorinated paraffin, piccolastic A-5, glycerol alpha-methyl alpha-phenyl ether, Halowax 1013, HB-40, monoamylphthalate, Nevilleac 10, o-nitrodiphenyl.

Additional plasticizers/release enhancers are known to a person skilled in the art.

It should be noted, that for the purpose of the present invention, the same compound may serve as a plasticizer and as a release enhancer, depending on the amount thereof in the composition. Thus, plasticizers are generally used in an amount of up to 10% by weight of the dry composition, more preferably from 0.5% to about 10% by weight of the dry composition. Release enhancers are generally used in an amount starting from 5% by weight of the dry composition, more preferably from about 5% to about 40% by weight of the dry composition.

The type and amount of the release enhancer and/or plasticizer determine the size and number of holes formed within the matrix upon the dissolution thereof in aqueous medium. The "Swiss cheese" type structure obtained is the key to the release behavior of the drug from the sustained release drug delivery system.

The terms "release enhancer" and "plasticizer" may also include materials which are classified as "pore formers". Suitable pore-formers include polyethylene glycol (PEG), PVP, PEO, HEC, HPMC and other aqueous-soluble cellulosics, water-soluble acrylate or methacrylate esters, polyacrylic acid and various copolymers and mixtures of these water soluble or water swellable polymers. Enteric polymers such as cellulose acetate phthalate (CAP) and HPMCAS are included in this class of polymers.

As can be seen in the Examples section which follows, a variety of release enhancers and/or plasticizers were used, either singly or in combination, in order to test the rapamycin release rates of each system. For example, glycerine is known to form relatively small voids, which will result in a slower release rate. The larger a PEG molecule is, the larger the voids formed and the higher the release rate that is expected. Klucels are cellulose ethers which are both water-soluble hydrophilic polymers, and also release enhancers in an aqueous environment.

Eudragit is also a hydrophilic polymer, which is pH dependant and therefore the solubility thereof changes as a function of the pH (more soluble in acidic conditions). Therefore, in this case there would be more voids, and hence larger release rates than under basic conditions.

As shown in the Examples section below, the inventors have now prepared novel sustained release drug delivery systems which are advantageous over presently known methods for the treatment of head and neck cancers and their prevention, such as: prolongation of therapeutic levels at the site of action that can lead to pharmacodynamic optimization of the treatment, improved patient compliance and decrease in expected adverse effects due to minimization of systemic exposure to the drug.

Thus, according to another aspect of the invention there is provided a sustained release drug delivery system, this system comprising:

a) a drug for the treatment of a head and neck cancer or for the prevention of the development of pre-malignant lesions to this cancer, and b) at least one polymer.

The sustained release drug delivery system of the invention is of the type that is characterized by adhesion and retention of the system to a surface in the oral cavity, for at least 1 hour, accompanied by release of the drug and maintaining an effective therapeutic concentration thereof in this cavity for at least 1 hour.

Preferably this is maintained for at least 4 hours, more preferably for at least 6 hours and most preferably for at least 8 hours.

The drug delivery system may be of the following types and forms: glued or physically-attached sustained release devices; mucoadhesive films/tablets and sustained release films. Preferably, the films are made of varnish compositions and/or gel compositions and/or foam compositions.

Varnish compositions for the preparation of sustained release films: varnishes are pharmaceutical solutions that are applied to surfaces, preferably hard surfaces, in the oral cavity (teeth, restorations, artificial teeth, braces, bracelets, retainers mouth guard piece) as a liquid precursor. After solvent evaporation a film containing the drug is formed, and releases the drug for at least 1 hour.

It should be noted that for varnishes all percentages refer to the dry film composition and not to the liquid precursor composition.

Varnishes are composed of at least one non-degradable hydrophobic polymer, a drug and a suitable volatile carrier, as described hereinabove.

In this case, it is necessary that the non-degradable hydrophobic polymer is a film-forming polymer.

Non limiting examples of suitable polymers for this purpose are one or more of the following: copolymer hydrogel of hydroxymethyl methacrylate (HEMA) and methylmethacrylate (MMA), ethylcellulose, sodium carboxymethyl cellulose, poly(acrylic acid), tragacanth, poly(methyl vinyl ether co-maleic anhydride), poly(ethylene oxide), methyl cellulose, sodium alginate, hydroxypropylmethylcellulose, karya gum, methylethylcellulose, soluble starch, gelatin, pectin, poly(vinyl pyrrolidone), poly(ethylene glycol), poly(vinyl alcohol), poly(hydroxyethylmethacrylate) and hydroxypropyl cellulose, Ethyl cellulose, Silicone rubber, polyethylene, polylactic acid, polymethylmethacrylate, gelatine and cross-linked derivatives, polyvinyl chloride, polyvinyl acetate, polyurethane.

The system may additionally include a plasticizer and/or a release enhancer.

Glued/physically-attached sustained release devices: these may include matrix tablets, capsules, micro or nano aggregates, devices based on osmotic pump principles, granulates, pellets, films, patches or membrane controlled devices which are small devices which can be glued onto the tooth tissue, or attached to the a tooth by other means (for example by a nylon suture) or any other soft tissue in the oral environment.

For this purpose the drug delivery system comprises at least one hydrophobic polymer and a drug, which are attached to the surface of the oral cavity either by a biocompatible glue, or by a physical device, as described hereinabove.

Non limiting examples of suitable polymers for this purpose are one or more of the following: copolymer hydrogel of hydroxymethyl methacrylate (HEMA) and methylmethacrylate (MMA), ethylcellulose, sodium carboxymethyl cellulose, poly(acrylic acid), tragacanth, poly(methyl vinyl ether co-maleic anhydride), poly(ethylene oxide), methyl cellulose, sodium alginate, hydroxypropylmethylcellulose, karya gum, methylethylcellulose, soluble starch, gelatin, pectin, poly(vinyl pyrrolidone), poly(ethylene glycol), poly(vinyl alcohol), poly(hydroxyethylmethacrylate) and hydroxypropyl cellulose, Ethyl cellulose, Silicone rubber, polyethylene, polylactic acid, polymethylmethacrylate, gelatine and cross-linked derivatives, polyvinyl chloride, polyvinyl acetate, polyurethane.

Mucoadhesive tablets/mucoadhesive films: these are mucoadhesive structures formulates as tablets or films may be used where the tablets/films containing the drug (such as sirolimus) and a mucoadhesive substance can be "stuck" in the mouth for at least 1 hour at various locations, releasing the drug to the salvia for at least 1 hour an accompanied with effective therapeutic concentration in saliva. The attachment may be on any oral (as defined) environment tissue (including both hard and soft tissues).

The mucoadhesive tablets/film may include matrix tablets, capsules, micro or nano aggregates, devices based on osmotic pump principles, granulates, pellets, films, patches or membrane controlled devices are small devices which can be glued onto the tooth tissue, or attached to the a tooth by other means (for example by a nylon suture) or any other (soft) tissue in the oral environment. Non limiting examples of suitable polymers are selected from a combination of copolymer hydrogel of hydroxymethyl methacrylate (HEMA) and methylmethacrylate (MMA), or composed solely of ethylcellulose the drug.

Sodium carboxymethyl cellulose, poly(acrylic acid), tragacanth, poly(methyl vinyl ether co-maleic anhydride), poly(ethylene oxide), methyl cellulose, sodium alginate, hydroxypropylmethylcellulose, karya gum, methylethylcellulose, soluble starch, gelatin, pectin, poly(vinyl pyrrolidone), poly(ethylene glycol), poly(vinyl alcohol), poly(hydroxyethylmethacrylate), hydroxypropyl cellulose, Ethyl cellulose, Silicone rubber, polyethylene, polylactic acid, polymethylmethacrylate, gelatine and cross-linked derivatives, polyvinyl chloride, polyvinyl acetate, polyurethane.

The method of the invention is applicable to both hard and soft surfaces in the oral cavity.

The term "soft surface", as used herein includes surfaces of the oral cavity selected from the lips, the pharynx, the tongue, the gingiva, the buccal mucosa, the bottom (floor) of the mouth under the tongue, the palate and the retromolar area.

The term "hard surface", as used herein includes surfaces of the oral cavity selected from natural teeth, restorations, artificial teeth, bracelets, retainers, mouth guard piece and braces.

As can be seen in the Examples section below, systems suitable for application on soft tissues are tablets. These are composed of either:

at least one hydrophobic polymer and a drug; to be attached to the surface with the aid of a suitable medical glue or placed in position with a suitable physical device.

OR—a mucoadhesive polymer and the drug.

The tablets may be prepared by either direct compression or by granulation, as known in the art.

The term "direct compression" is defined as the process by which tablets are compressed directly from powder mixture of the active ingredient (drug) with suitable excipients. No pretreatment of the powder blend by wet or dry granulation procedure is required. The process is done by simple mixing of the active ingredient (drug) with suitable additive and compression to tablets.

The term "granulation" refers to a process of size-enlargement, where primary powder particles are gathered into larger, semi-permanent aggregates (granules) in which the original particles can still be identified. Pharmaceutical granules typically have a size range of 0.1 to 2 mm and the majority will be used as an intermediate product in the production of tablets, while some granulations will be dispensed as such in packets or in capsules. The main granulation methods are dry and wet granulation. Via dry granulation powders are compacted under high pressure using (a) slugging to produce a large tablet ('slug') in a heavy-duty tabletting machine or (b) roller compaction to compact the powder between two rollers into a material sheet. After both processes the compacted material is broken up by milling to produce the granular material. This dry method can be used for drugs sensitive to moisture and heat. Wet granulation occurs when powders are mixed with a liquid phase, which acts as a binder during the granulation process. The most commonly used techniques in the pharmaceutical industry are fluid bed granulation and high-shear granulation.

In either case, the system may additionally include a plasticizer and/or a release enhancer.

By one preferred embodiment the drug delivery system is a sustained release film, formed of a varnish.

In order to form the film, there is provided a method wherein the sustained release delivery system is administered by applying on the surface of the oral cavity a liquid precursor composition capable of forming, upon solidification thereof on the surface, a film which forms a sustained release drug delivery system, comprising a drug, at least one non-degradable hydrophobic film-forming polymer, as those have been described hereinabove, and a pharmaceutically acceptable volatile carrier.

Thus, according to another aspect of the invention there is also provided a liquid precursor varnish composition, for forming upon solidification thereof on a surface in the oral cavity, a film which forms a sustained release drug delivery system, this composition comprising:
  a) a drug for the treatment of a head and neck cancer or for the prevention of the development of pre-malignant lesions to this cancer;
  b) at least one non-degradable hydrophobic film-forming polymer; and
  c) a pharmaceutically acceptable volatile carrier;
such that the sustained release drug delivery system can be attached to the surface and remain attached thereto for at least 1 hour, accompanied by release of the drug and maintaining an effective therapeutic concentration thereof in the cavity, for at least 1 hour.

The term "liquid" refers to a composition which is fluid at room temperature when present in the vessel.

The term "liquid precursor" means that while the composition of the invention is initially liquid, upon application to a hard tissue it solidifies mainly due to evaporation of the solvent.

Given the special needs in applying the liquid precursor varnish composition in the oral cavity, it is necessary to limit the viscosity of this varnish composition to an acceptable working range.

It has been found by the inventors that preferably, the composition described herein should have a viscosity ranging from about 10 centipoises to about 3,500 centipoises, to achieve this purpose.

In particular, the present invention concerns a liquid precursor varnish composition suitable for the treatment of oral cancer, in particular for the treatment of head and neck squamous cell carcinoma (HNSCC).

The drug suitable for this purpose is described hereinbefore. Preferably, the drug is an inhibitor of mTOR, more preferably rapamycin and/or any of its analogues, as described hereinabove.

The solvent (at times referred to as "carrier") is usually a biocompatible and volatile at body temperature hydroalcoholic or alcoholic solvent, such as ethanol.

The carrier suitable to be used for the varnish composition should be capable of evaporating under conditions normally present in the oral cavity, optionally capable of evaporation under application of active drying conditions (such as under heat air flow).

The solidification of the liquid precursor of the invention into a solid matrix film can take place naturally by allowing the solvent to evaporate or can be facilitated by applying gentle heat, air flow to the mouth.

The term "sustained release varnish" refers to a varnish (in the present invention in a liquid form that forms a film matrix) that allows the drug (such as sirolimus) contained therein to transfer to the oral cavity over a prolonged period of time typically of at least 1 hour accompanied with effective therapeutic concentration in saliva. Typically the composition in the solid form is resistant to some degree to erosion caused by normal activities such as eating, drinking brushing teeth etc.

The liquid precursor composition is to be applied (by brushing, dipping, spraying etc) on hard tissues and is not intended to be applied on soft tissues such as the gingiva, the tongue, the palate etc.

The at least one hydrophobic polymer is preferably selected from: cross linked polymers and derivatives of polymers such as Ethyl cellulose, Silicone rubber, polyethylene, polylactic acid, polymethylmethacrylate, gelatin and cross-linked derivatives, polyvinyl chloride, polyvinyl acetate, polyurethane. Preferably the composition of the invention comprises Ethyl Cellulose as an example of a hydrophobic polymer.

The invention also concerns the embodiment of the above-described composition further comprising a vehicle selected from the group consisting of; ethyl alcohol; and ethyl alcohol and water.

The invention also concerns the embodiment of the above-described composition which additionally contains a plasticizer or release enhancer as described hereinabove, for example polyethylene glycol, dibutyl phthalate glycerol, tributhyl citrate, triethyl citrate or Triacetine).

The invention also concerns an embodiment of the above described composition further comprising a taste denoting or taste masking agent.

The varnish composition may be applied directly in the form of a film, a gel or a foam, by brushing, immersing, soaking, spraying on the relevant part of the teeth, oral tissues implants or any oral appliances or devices for dental or non dental use.

By another preferred embodiment, the present invention concerns a mucoadhesive tablet or a mucoadhesive film that can be placed in the mouth on a soft or hard tissue (oral tissues) or a hard or soft surface, as described in detail hereinabove.

The following is a brief description of the drawings.

EXPERIMENTAL

Materials and Methods

Rapamycin was obtained from LC Laboratories Woburn, Mass., USA. Ethylcellulose (EC) was obtained from (Ethocel premium N100) was purchased from Dow Chemical Company, Russellville, Ark., USA.

PEG 400 and PEG 3350 ware purchased from Merck, Germany. Carbopol (mucoadhesive agent) was obtained from Noveon Inc. (OH, USA).

All other chemicals were obtained from known vendors, such as Merck and Sigma-Aldrich.

Quantification of rapamycin was performed utilizing HPLC UV analytical method. For this purpose, an HP 1090 apparatus equipped with UV detector equipped with Inertsil ODS-80A column (5 um 150×4.6 mm GL Science, Tokyo, Japan, was used. The mobile phase was 82% methanol, 17.9% water and 0.1% of acetic acid, at 1 ml/min flow.

All experiments were performed in triplicates.

Teflon molds (0.7 cm diameter) were specially made for the purpose of the invention.

Tablets were prepared by using a laboratory press fitted with a 3 mm flat-faced punch, applying a pressure of 3 tons.

RESULTS

Rapamycin stability was evaluated by sampling known concentration solutions at 37° C. for 24 hours. No stability problems were observed.

Following necessary physicochemical characterization was performed the proposed drug delivery systems were formulated.

Example 1A: Preparation of Sustained Release Varnishes of Rapamycin

Sustained release varnishes of Rapamycin were prepared by dissolving rapamycin, ethyl cellulose (EC) and PEG 400 in ethanol, according to the quantities given in table 1. After homogenous solutions were obtained (after stirring overnight), the solutions were casted into Teflon molds and allowed to dry completely overnight at room temperature to form a film. The mean thickness of films was 147 μm.

TABLE 1A

| Formulation | Ingredient | Amount of ingredient in solution (g) | Concentration of ingredient in dry film (%) |
|---|---|---|---|
| RAPA-1 | Ethyl cellulose | 0.27 | 42.19 |
|  | PEG 400 | 0.03 | 4.69 |
|  | Rapamycin | 0.34 | 53.13 |
|  | Ethanol | 6 cc |  |
| RAPA-2 | Ethyl cellulose | 0.35 | 35.00 |
|  | PEG 400 | 0.025 | 2.50 |
|  | Klucel EF | 0.125 | 12.50 |
|  | Rapamycin | 0.5 | 50.00 |
|  | Ethanol | 5 cc |  |
| RAPA-3 | Ethyl cellulose | 0.2019 | 28.09 |
|  | PEG 400 | 0.02644 | 3.68 |
|  | Klucel EF | 0.2019 | 28.09 |
|  | Rapamycin | 0.2884 | 40.13 |
|  | Ethanol | 5 cc |  |
| RAPA-4 | Ethyl cellulose | 0.139 | 36.87 |
|  | PEG 400 | 0.038 | 10.08 |
|  | Rapamycin | 0.2 | 53.05 |
|  | Ethanol | 6 cc |  |
| RAPA-5 | Ethyl cellulose | 0.064 | 16.98 |
|  | PEG 400 | 0.113 | 29.97 |
|  | Rapamycin | 0.2 | 53.05 |
|  | Ethanol | 6 cc |  |
| RAPA-6 | Ethyl cellulose | 0.1015 | 26.92 |
|  | PEG 400 | 0.0755 | 20.03 |
|  | Rapamycin | 0.2 | 53.05 |
|  | Ethanol | 6 cc |  |

In vitro release of rapamycin from these compositions was determined by immersing the films in 15-25 cc 5% Sodium lauryl sulfate (SLS) in $H_2O$ at 37° C. 0.6 cc samples were withdrawn and rapamycin concentration was determined by Utilizing HPLC. The results show that, as desired, a SR release profile is obtained from all DDSs while 20% PEG 400 formulation exhibits the highest absolute release.

Example 1B: Preparation of Modified Sustained Release Varnish Compositions of Rapamycin The influence of different formulatory alternations on cumulative release profiles of rapamycin from sustained release (SR) varnish drug delivery systems (DDS's) was tested. The SR DDS's were prepared by dissolving the active ingredient rapamycin, a polymer (ethyl cellulose, EC) and optionally release modifiers (PEG 400, Klucel EF, Klucel HF, Eudragit and glycerine) in absolute ethanol, according to the quantities given in Table 1B. After a homogenous solution was obtained it was brushed on a hydroxylapatite (HA) surface (substrate).

TABLE 1B

| Formulation | Ingredient | Amount of ingredient in solution (g) | Concentration of ingredient in dry film (%) |
|---|---|---|---|
| For. 22E | Rapamycin | 0.112 | 20 |
|  | PEG 400 | 0.168 | 30 |
|  | Ethyl cellulose | 0.28 | 50 |
|  | Ethanol | 4 cc |  |
| For. 24 | Rapamycin | 0.168 | 30 |
|  | PEG 400 | 0.168 | 30 |
|  | Ethyl cellulose | 0.224 | 40 |
|  | Ethanol | 4 cc |  |
| For. 25 | Rapamycin | 0.168 | 30 |
|  | PEG 400 | 0.168 | 30 |
|  | Klucel EF | 0.056 | 10 |
|  | Ethyl cellulose | 0.168 | 30 |
|  | Ethanol | 4 cc |  |
| For. 26 | Rapamycin | 0.168 | 30 |
|  | PEG 400 | 0.168 | 30 |
|  | Klucel EF | 0.112 | 20 |
|  | Ethyl cellulose | 0.112 | 20 |
|  | Ethanol | 4 cc |  |
| For. 27 | Rapamycin | 0.168 | 30 |
|  | PEG 400 | 0.168 | 30 |
|  | Klucel EF | 0.084 | 15 |
|  | Ethyl cellulose | 0.14 | 25 |
|  | Ethanol | 4 cc |  |
| For. 28 | Rapamycin | 0.168 | 30 |
|  | PEG 400 | 0.168 | 30 |
|  | Klucel HF | 0.056 | 10 |
|  | Ethyl cellulose | 0.168 | 30 |
|  | Ethanol | 4 cc |  |
| For. 29 | Rapamycin | 0.168 | 30 |
|  | PEG 400 | 0.168 | 30 |
|  | Klucel HF | 0.084 | 15 |
|  | Ethyl cellulose | 0.14 | 25 |
|  | Ethanol | 6 cc |  |
| For. 30 | Rapamycin | 0.168 | 30 |
|  | PEG 400 | 0.168 | 30 |
|  | Klucel HF | 0.112 | 20 |
|  | Ethyl cellulose | 0.112 | 20 |
|  | Ethanol | 6 cc |  |
| For. 31 | Rapamycin | 0.168 | 30 |
|  | PEG 400 | 0.168 | 30 |

TABLE 1B-continued

| Formulation | Ingredient | Amount of ingredient in solution (g) | Concentration of ingredient in dry film (%) |
|---|---|---|---|
| | Eudragit L100 | 0.056 | 10 |
| | Ethyl cellulose | 0.168 | 30 |
| | Ethanol | 4 cc | |
| For. 32 | Rapamycin | 0.168 | 30 |
| | PEG 400 | 0.168 | 30 |
| | Eudragit L100 | 0.14 | 25 |
| | Ethyl cellulose | 0.084 | 15 |
| | Ethanol | 4 cc | |
| For. 33 | Rapamycin | 0.168 | 30 |
| | PEG 400 | 0.168 | 30 |
| | Eudragit L100 | 0.112 | 20 |
| | Ethyl cellulose | 0.112 | 20 |
| | Ethanol | 4 cc | |
| For. 34 | Rapamycin | 0.168 | 30 |
| | Ethyl cellulose | 0.392 | 70 |
| | Ethanol | 4 cc | |
| For. 35 | Rapamycin | 0.168 | 30 |
| | Glycerine | 0.056 | 10 |
| | Ethyl cellulose | 0.336 | 60 |
| | Ethanol | 4 cc | |
| For. 36 | Rapamycin | 0.168 | 30 |
| | Glycerine | 0.168 | 30 |
| | Ethyl cellulose | 0.224 | 40 |
| | Ethanol | 3 cc | |
| For. 37 | Rapamycin | 0.168 | 30 |
| | Glycerine | 0.112 | 20 |
| | Ethyl cellulose | 0.28 | 50 |
| | Ethanol | 4 cc | |
| For. 38 | Rapamycin | 0.168 | 30 |
| | Glycerine | 0.224 | 40 |
| | Ethyl cellulose | 0.168 | 30 |
| | Ethanol | 2.5 cc | |

SR DDS's in vitro release profiles experiments were conducted by immersing the prepared substrate in 25 ml trizma base buffer pH 7.0 containing 5% SLS under sink conditions. The release medium was sampled at 0.5, 1, 1.5, 2, 3, 4, 5, 6, 7, 8 and 24 hours time points and rapamycin concentrations were analytically determined. The results are summarized in FIGS. 1-4.

Example 2: Preparation of Sustained Release Tablets of Rapamycin

Sustained release tablets were prepared either by mixing rapamycin, a hydrophobic polymer (ethyl cellulose), and optionally a release modifier (PEG 3350), or by mixing rapamycin, a mucoadhesive polymer (such as carbopol), and optionally a release modifier (PEG 3350), according to the quantities given in table 2, whereas the mixing was done by a geometric dilution method.

Then the obtained mixture was pressed under the pressure of 3 tons force to obtain 3 mm diameter 30 mg tablets.

TABLE 2

| Formulation | Ingredient | Amount of ingredient per tablet (mg) | Amount of ingredient per tablet (%) |
|---|---|---|---|
| Tab-1 | Ethyl cellulose | 25 | 83.33 |
| | Klucel EF | 3 | 10.00 |
| | Rapamycin | 2 | 6.67 |
| Tab-2 | Ethyl cellulose | 19 | 63.33 |
| | Klucel EF | 9 | 30.00 |
| | Rapamycin | 2 | 6.67 |
| Tab-3 | Ethyl cellulose | 25 | 83.33 |
| | PEG 3350 | 3 | 10.00 |
| | Rapamycin | 2 | 6.67 |
| Tab-4 | Ethyl cellulose | 19 | 63.33 |
| | PEG 3350 | 9 | 30.00 |
| | Rapamycin | 2 | 6.67 |
| Tab-5 | Ethyl cellulose | 19 | 63.33 |
| | PEG 3350 | 9 | 30.00 |
| | Rapamycin | 2 | 6.67 |
| Tab-6 | Ethyl cellulose | 19 | 63.33 |
| | Klucel EF | 9 | 30.00 |
| | Rapamycin | 2 | 6.67 |
| Tab-7 | Ethyl cellulose | 26.5 | 88.33 |
| | Klucel EF | 1.5 | 5.00 |
| | Rapamycin | 2 | 6.67 |
| Tab-8 | Ethyl cellulose | 26.5 | 88.33 |
| | PEG 3350 | 1.5 | 5.00 |
| | Rapamycin | 2 | 6.67 |
| Tab-9 | Carbopol | 26.5 | 88.33 |
| | PEG 3350 | 1.5 | 5.00 |
| | Rapamycin | 2 | 6.67 |
| Tab-10 | Carbopol | 22 | 73.33 |
| | PEG 3350 | 6 | 20.00 |
| | Rapamycin | 2 | 6.67 |

Figure 1:
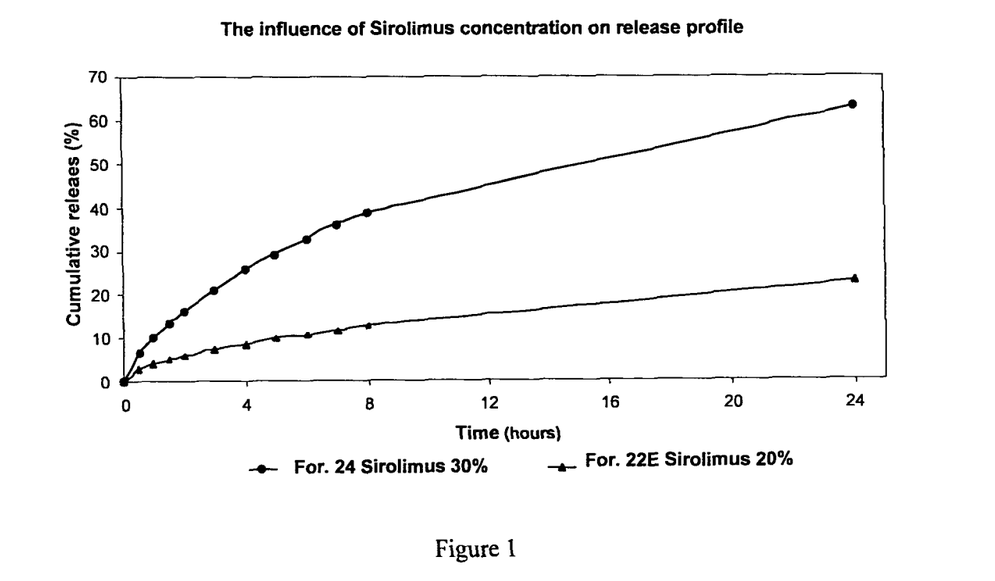
FIG. 1 is a graph presenting the influence of Sirolimus (rapamycin) concentration on the rapamycin release profile of a varnish prepared according to preferred embodiments of the invention.
Figure 2:
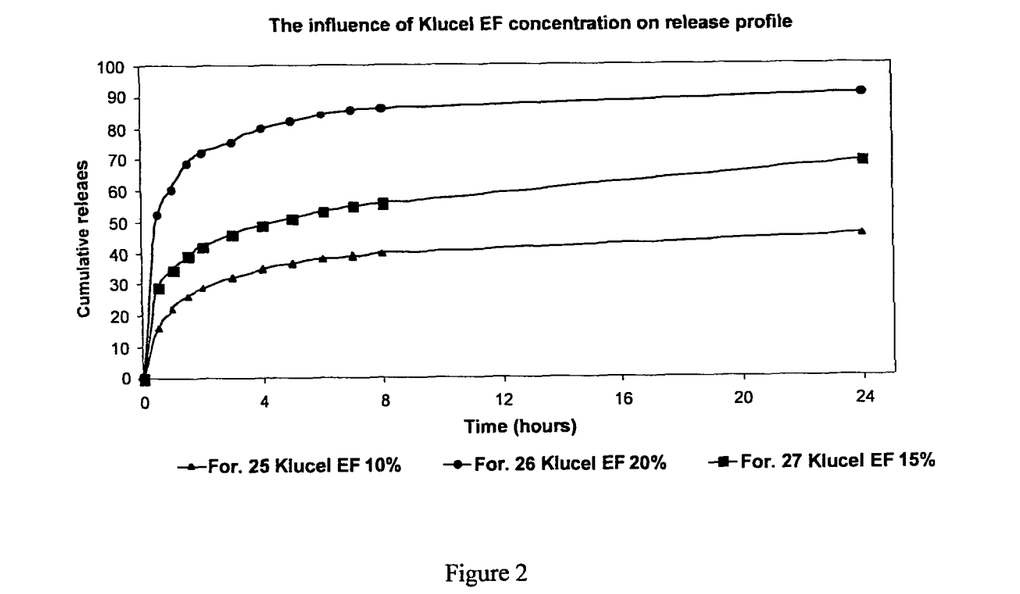
FIG. 2 is a graph presenting the. influence of Klucel EF concentration on the rapamycin release profile of a varnish prepared according to preferred embodiments of the invention.
Figure 3:
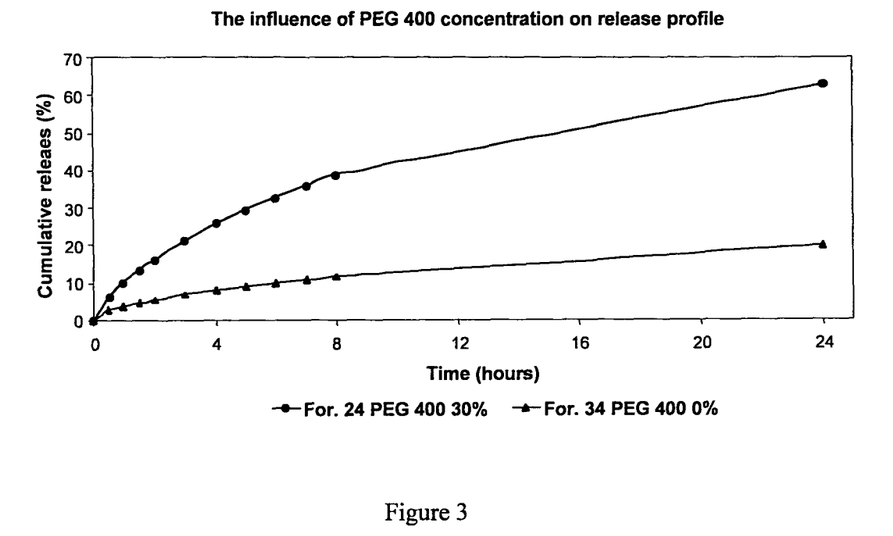
FIG. 3 is a graph presenting the influence of PEG 400 concentration on the rapamycin release profile of a varnish prepared according, to preferred embodiments of the invention.
Figure 4:
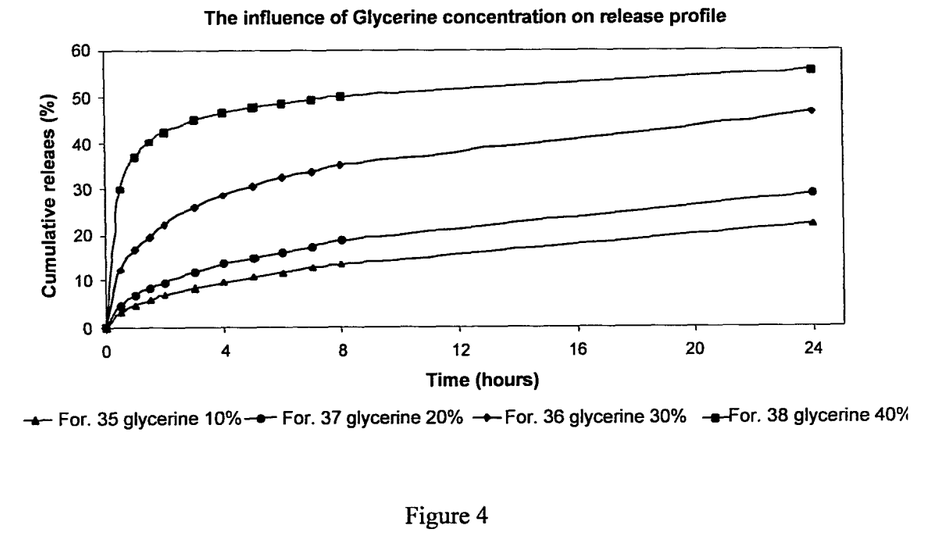
FIG. 4 is a graph presenting the influence of Glycerine concentration on the rapamycin release profile of a varnish prepared according to preferred embodiments of the invention.
Figure 5:
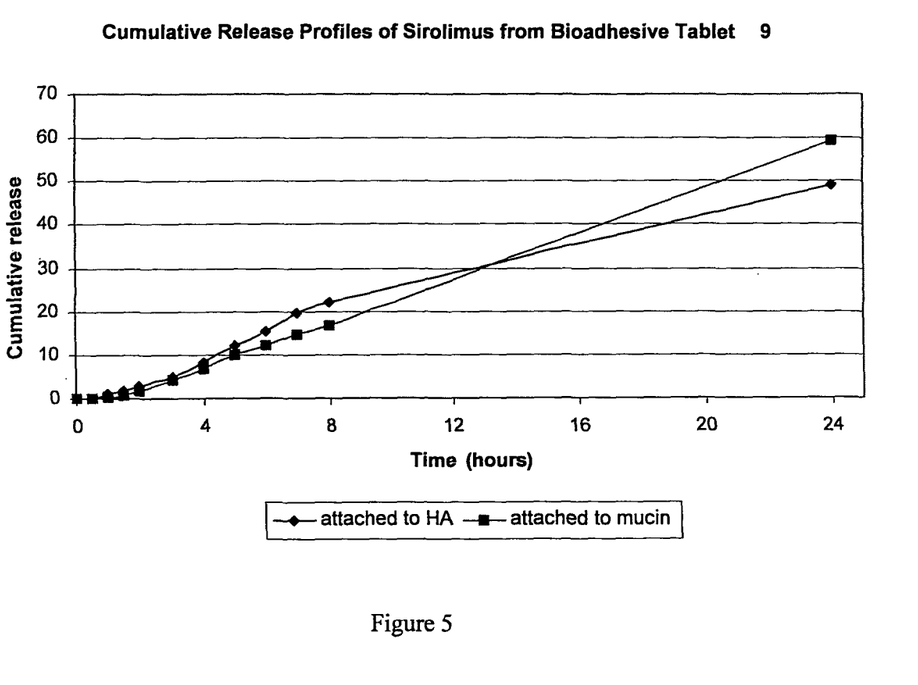
FIG. 5 is a graph presenting the Cumulative release of Rapamycin, according to preferred embodiments of the invention, from adhesive tablet 9 on HA and Mucin in Trizma base 50 mM pH=6.9+5% SLS.

In vitro release of rapamycin from tablets was determined by attaching the tablets to Hydroxylapatite (HA) like surface or to mucin tablets in 20-25 cc Trizma base 50 mM at pH—6.8 with 5% SLS at 37° C. 0.6 cc samples were withdrawn and rapamycin concentration was determined as mentioned above. Exemplary results are presented in FIG. 5, showing that, as desired, a SR release profile is obtained.

The invention claimed is:
1. A film-forming medicated oral varnish composition suitable for application on a hard surface of the oral cavity and for local delivery of rapamycin and/or its analogues therein, said composition, comprising:
   a) rapamycin and/or its analogues;
   b) ethyl cellulose; and
   c) a pharmaceutically acceptable volatile carrier selected from the group consisting of ethyl alcohol and a mixture of ethyl alcohol and water,
   wherein ethyl alcohol is 77.9% to 92.6% w/w of said composition, rapamycin and/or its analogues constitutes from about 10% dry weight to about 40% dry weight of the composition, and ethyl cellulose constitutes from about 60% dry weight to about 90% dry weight of the composition, and wherein the amounts of the components of the composition are so selected such that the composition will have the properties that, upon solidification thereof on said hard surface in the oral cavity, there will be formed a sustained release drug delivery system in the form of a film retainable on said hard surface for at least 1 hour, releasing rapamycin and/or its analogues, and maintaining an effective therapeutic concentration thereof in said cavity for at least 1 hour.

2. The composition of claim 1 having a viscosity ranging from about 10 centipoises to about 3,500 centipoises.

3. The composition of claim 1, further comprising at least one plasticizer and/or at least one release enhancer.

4. The composition of claim 3, wherein said plasticizer or said release enhancer is selected from the group consisting of polyethylene glycol, dibutyl phthalate, glycerol, tributyl citrate, triethyl citrate and triacetin.

5. The composition of claim 1, further comprising a taste denoting or taste masking agent.

6. A method of treating a head and neck cancer or stopping or slowing the development of pre-malignant lesions into head and neck cancer, said method comprising: administering locally to the oral cavity of a subject having head or neck cancer or having a pre-malignant lesion, a film-forming medicated oral varnish composition according to claim 1 by applying said composition onto a hard surface of the oral cavity of the subject so as to form a sustained release drug delivery system in the form of a film retainable on said hard surface for at least 1 hour, releasing rapamycin and/or its analogues, and maintaining an effective therapeutic concentration thereof in said cavity, for at least 1 hour.

7. The method according to claim 6, wherein said film-forming medicated oral varnish composition further comprises a plasticizer and/or a release enhancer.

8. The method according to claim 6 wherein said subject has a head and neck cancer and wherein said head and neck cancer is an oral cancer.

9. The method according to claim 8 wherein said oral cancer is a carcinoma.

10. The method according to claim 9 wherein said carcinoma is a head and neck squamous cell carcinoma (HNSCC).

11. A method according to claim 8, wherein said cancer is a melanoma cancer.

12. The method according to claim 6, wherein said surface in said oral cavity is selected from natural teeth, restorations, artificial teeth, bracelets, retainers, mouth guard piece and braces.

13. The method of claim 6, wherein said composition is applied by brushing, dipping or spraying onto said surface.

14. The composition of claim 3, wherein said at least one release enhancer comprises, a copolymer of methacrylic acid and methyl methacrylate.

15. A film-forming liquid precursor varnish composition comprising:
   a) rapamycin and/or its analogues;
   b) ethyl cellulose; and
   c) a pharmaceutically acceptable volatile carrier selected from the group consisting of ethyl alcohol and a mixture of ethyl alcohol and water,
   wherein ethyl alcohol is 77.9% to 92.6% w/w of said composition, rapamycin and/or its analogues constitutes from about 10% dry weight to about 40% dry weight of the composition, and ethyl cellulose constitutes from about 60% dry weight to about 90% dry weight of the composition, and wherein the amounts of the components of the precursor composition are so selected such, upon forming a film after solidification thereof on a surface of the oral cavity, such film will have the properties of a sustained delivery system that remains attached to the surface for at least 1 hour, accompanied by release of said drug, and maintaining an effective therapeutic concentration thereof in said oral cavity for at least 1 hour; and wherein the amounts of the components of the precursor composition are so selected such that, upon forming a film by solidification thereof on a hard substrate under sink conditions at 37° C., said drug is released at an extent not exceeding about 20% at 24 hours.

* * * * *